United States Patent
Carrola, Jr. et al.

(10) Patent No.: US 9,218,660 B2
(45) Date of Patent: Dec. 22, 2015

(54) MACHINE VISION SYSTEMS AND METHODS FOR ANALYSIS AND TRACKING OF STRAIN IN DEFORMABLE MATERIALS

(71) Applicant: Southwest Research Institute, San Antonio, TX (US)

(72) Inventors: John T. Carrola, Jr., San Antonio, TX (US); Warren Carl Couvillion, Jr., San Antonio, TX (US); Susan M. Porter, San Antonio, TX (US); David R. Chambers, San Antonio, TX (US); Christopher J. Guerra, San Antonio, TX (US)

(73) Assignee: SOUTHWEST RESEARCH INSTITUTE, San Antonio, TX (US)

( * ) Notice: Subject to any disclaimer, the term of this patent is extended or adjusted under 35 U.S.C. 154(b) by 168 days.

(21) Appl. No.: 14/208,941

(22) Filed: Mar. 13, 2014

(65) Prior Publication Data
US 2015/0262352 A1    Sep. 17, 2015

(51) Int. Cl.
| | |
|---|---|
| *G06K 9/00* | (2006.01) |
| *G06T 7/00* | (2006.01) |
| *G01L 1/06* | (2006.01) |
| *G01L 1/24* | (2006.01) |
| *G01B 11/16* | (2006.01) |
| *H04N 5/33* | (2006.01) |
| *G06T 7/60* | (2006.01) |
| *G06K 9/46* | (2006.01) |
| *G06K 9/62* | (2006.01) |

(52) U.S. Cl.
CPC ............ *G06T 7/0012* (2013.01); *G01B 11/168* (2013.01); *G01L 1/06* (2013.01); *G01L 1/248* (2013.01); *G06K 9/00624* (2013.01); *G06K 9/4642* (2013.01); *G06K 9/6267* (2013.01); *G06T 7/60* (2013.01); *H04N 5/33* (2013.01)

(58) Field of Classification Search
CPC ........ G01B 11/168; G01L 1/06; G01L 1/248; G06K 9/00624; G06K 9/4642; G06K 9/6267; G06T 7/0012; G06T 7/60; H04N 5/33
See application file for complete search history.

(56) References Cited

U.S. PATENT DOCUMENTS

| | | | |
|---|---|---|---|
| 7,892,188 B2 * | 2/2011 | Walker ................. | A61B 5/0048 600/368 |
| 2007/0116766 A1 * | 5/2007 | Amick .................... | A61L 27/52 424/486 |
| 2008/0241209 A1 * | 10/2008 | Arruda ................ | A61L 27/3608 424/423 |

OTHER PUBLICATIONS

Pavan et al, "Ultrasound-based transient elastography using a magnetic excitation", 2012 IEEE International Ultrasonics Symposium Proceedings, pp. 1846-1849.*

* cited by examiner

*Primary Examiner* — Amara Abdi
(74) *Attorney, Agent, or Firm* — Grossman, Tucker et al

(57) ABSTRACT

A method and system for analysis of a viscoelastic response in a deformable material. The system includes a light source configured to provide linearly polarized light and a polariscope configured to receive said linearly polarized light and to generate an image associated with a viscoelastic response of said deformable material. The system also includes a machine vision system configured to operate on the image to locate the response on the deformable material and to classify the response as one of a plurality of predefined types of responses. A display may then be provide that is configured to provide feedback of the location of the viscoelastic response and classification of the response to a user of said system.

26 Claims, 9 Drawing Sheets

MACHINE VISION SYSTEMS AND METHODS FOR ANALYSIS AND TRACKING OF STRAIN IN DEFORMABLE MATERIALS

GOVERNMENT SUPPORT CLAUSE

This invention was made with United States Government support under Contact No. W911QX-12-C-0146 awarded by the U.S. Army. The Government has certain rights in this invention.

FIELD OF INVENTION

The present disclosure relates to analysis and tracking of strain in deformable materials, and in particular to machine vision based analysis and tracking of strain in deformable materials with application to simulation and training for medical or surgical procedures.

BACKGROUND

The detection and simulation of interactions with deformable objects is a relatively difficult but important problem in the field of simulation. For example, the actions of a surgeon are generally guided, to a large extent, by feeling or tactile feedback from the interaction between the surgeon's fingers or tools and the body tissue being operated upon. It would be useful, however, during surgical training, to use a deformable material as a substitute for human tissue, or other body parts, and to enable the teacher to monitor the characteristics of these interactions by the student in a non-intrusive manner.

Unfortunately, however, the attachment or insertion of sensors into objects that are intended to simulate tissue, such as, for example, ballistics gel, can affect the objects' stiffness and detract from the fidelity of the simulation. The insertion of sensors may also increase the cost of the objects, and decrease the simulation availability due to the need to swap out the objects between sessions. Interactions that require cutting the deformable objects can also damage the sensors. There is a need, therefore, for a method or system capable of tracking interactions with deformable objects that does not require attaching or inserting sensors into either the soft, deformable objects or the tools/objects that are interacting with them.

SUMMARY

A system for analysis of a viscoelastic response in a deformable material, said system comprising a light source configured to provide linearly polarized light and a polariscope configured to receive the linearly polarized light and to generate an image associated with a viscoelastic response of the deformable material, wherein the deformable object comprises a viscoelastic, transparent, thermoplastic, birefringent material. The system also includes a machine vision system configured to operate on the image to locate the response on the deformable material and to classify the response as one of a plurality of predefined types of responses. The system also includes a display configured to provide feedback of the location of the viscoelastic response and the classification of the response to a user of said system.

In method form, the present invention comprises a method for analysis of a viscoelastic response in a deformable material comprising providing linearly polarized light to a polariscope and generating an image from the polariscope, the image associated with a viscoelastic response of the deformable material, wherein the deformable material comprises a viscoelastic, transparent, thermoplastic birefringent material. This is then followed by locating the viscoelastic response on the deformable material, based on the image and classifying the response as one of a plurality of responses, based on the image. This may then be followed by providing feedback of the location of the viscoelastic response and classification of the response to a user.

In a still further related embodiment, the present invention comprises an article comprising a non-transitory storage medium having stored thereon instructions that when executed by a machine result in the following operations on a deformable material: providing linearly polarized light to a polariscope and generating an image from the polariscope, the image associated with a viscoelastic response of the deformable material, wherein the deformable material comprises a viscoelastic, transparent, thermoplastic birefringent material. This is then followed by locating the viscoelastic response on the deformable material, based on the image and classifying the response as one of a plurality of responses, based on said image. This may then be followed by providing feedback of the location of the viscoelastic response and classification of the response to a user.

BRIEF DESCRIPTION OF DRAWINGS

The above-mentioned and other features of this disclosure, and the manner of attaining them, will become more apparent and better understood by reference to the following description of embodiments described herein taken in conjunction with the accompanying drawings, wherein.

DETAILED DESCRIPTION OF PREFERRED EMBODIMENTS

Figure 1:
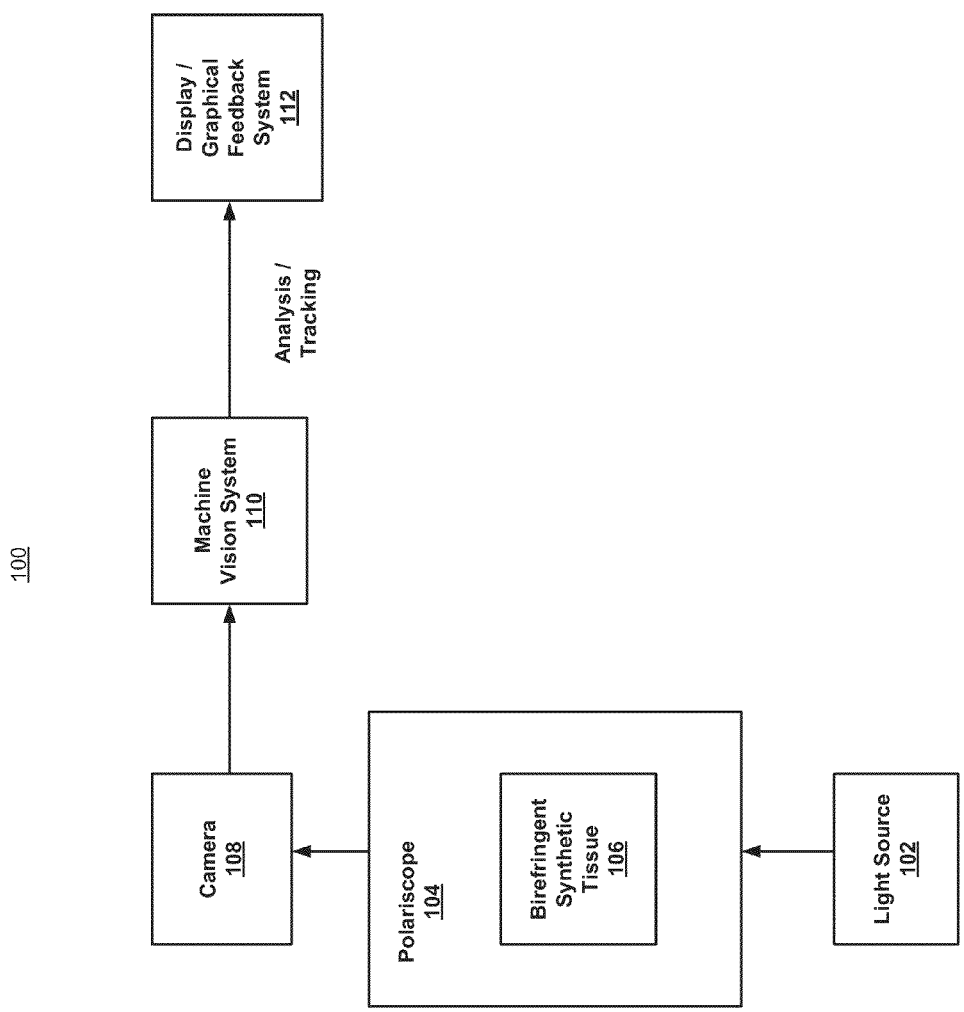
FIG. 1 illustrates a top level system block diagram of one example embodiment consistent with the present disclosure.

It may be appreciated that the present disclosure is not limited in its application to the details of construction and the arrangement of components set forth in the following description or illustrated in the drawings. The invention(s) herein may be capable of other embodiments and of being practiced or being carried out in various ways. Also, it may be appreciated that the phraseology and terminology used herein is for the purpose of description and should not be regarded as limiting as such may be understood by one of skill in the art.

Throughout the present description, like reference characters may indicate like structure throughout the several views, and such structure need not be separately discussed. Furthermore, any particular feature(s) of a particular example embodiment may be equally applied to any other example embodiment(s) of this specification as suitable. In other words, features between the various example embodiments described herein are interchangeable, and not exclusive.

The present disclosure relates to machine vision based analysis and tracking of strain in deformable materials with application to simulation and training for medical or surgical procedures. A deformable material suitable for use herein is understood as a material that is capable of being deformed in response to an applied stress, which response may comprise a viscous response (non-recovable) or elastic response (recoverable). That is, the material is preferably viscoelastic. More preferably, the material is one that resembles anatomical tissue, such that the present invention may be advantageously applied to monitoring the effects of manipulation on the deformable material without the need to either attach or insert, into the materials, any sensors. In addition, the deformable materials are such that they indicate birefrigence whereupon a ray of light passing through such material has its electromagnetic wave components resolved along two stress directions (perpendicular to the light direction) and each of these components experiences different refractive indices. Accordingly, the deformable material herein includes any material that will exhibit birefrigence to polarized light.

In addition the deformable material herein is one that is transparent in the sense that it exhibits optical property changes that are sufficient for viewing by cameras that may proceed in conjunction with computer aided detection. Furthermore, the transparency is such that a user may then observe visual changes provided by the computer aided detection that is conveniently output to a computer screen terminal.

Preferred deformable materials herein are preferably formed from thermoplastic block copolymers and an oil, as described in U.S. Publication No. 2007/0116766, whose teachings are incorporated by reference. Block copolymers are generally composed of sequences of the same monomer unit as one block-type, covalently bound to unlike sequences as another block-type. The blocks can be connected in a variety of ways. The different blocks can sometimes intermix freely at sufficiently high temperature, or when sufficiently diluted with solvent, generating a more disordered form. However, it is common for the blocks to spontaneously self-assemble ("order") into a diversity of mesophases, with the size scale governed by the chain dimensions (order may be tens of nanometers). In the mesophases, dissimilar (e.g., thermodynamic dissimilarity) blocks exist in distinct "microdomains" which are highly enriched in blocks of the same type, sometimes to the point of being essentially pure. The covalent bonds linking the dissimilar blocks are thus localized to the vicinity of the microdomain interfaces. The block ratio is easily varied during polymer synthesis to alter the mesophase structure.

Particularly suitable polymers for use herein are thermoplastic block co-polymers that are based on at least two relatively thermodynamically incompatible or dissimilar block segments. Many kinds of styrenic block copolymers are contemplated to be suitable. Hydrogenated styrenic block copolymers are contemplated to be particularly suitable. The following block copolymers are specifically contemplated: styrene-butadiene-styrene polymers; styrene-isoprene-styrene polymers; styrene-ethylene-butylene-styrene polymers; styrene-ethylenepropylene polymers; styrene-ethylenebutylene polymers; styrene-butadiene polymers; and styrene-isoprene polymers. One or more of the blocks may be a random copolymer.

Suitable oils in which the block copolymers may be mixed with or dispersed in include: mineral oils and other hydrocarbon oils; organic oils (vegetable and animal based), synthetic oils similar to any of the foregoing, and mixtures thereof. The level of block copolymer may preferably be present in an amount of 12 wt. % to 22 wt. %, with the remainder being the oil (i.e. oil present at a level of 88 wt. % to 78 wt. %).

Another feature of the deformable materials noted above is their ability to be resued. That is, after deformation, the deformable materials are reusable such that they may be heated and reformed and configured into another shape for a different testing protocol. As noted below, this is another characteristic of the feature that the deformable materials are, as noted above, preferably derived from thermoplastic block copolymers. Thermoplastic is to be understood herein as a material that can be repeatedly heated and shaped.

The deformable materials herein are also such that they simulate the density and viscosity of human and animal muscle tissue. For example, the density of human muscle tissue is about 1.0599 g/cm$^3$. Accordingly, the deformable materials herein may preferably have a density in the range of 1.03 g/cc to 1.07 g/cc. Therefore, the deformable materials herein provide an approximation of muscle tissue and provide useful performance for ballistic testing.

Accordingly, a deformable object may now be used to model anatomical tissue or other body structures. As stress or strain regions are induced in the deformable material, for example due to manual manipulation, the application of tools such as scalpels or clamps, or any other types of interactions, birefringence patterns are generated which may be imaged by a polariscope. A machine vision system, for example, a system including a trainable classifier, may be configured to locate, recognize and/or identify these interactions with the deformable material. For example a scalpel incision may be recognized along with the speed and depth of the cut. Information related to any characteristics of the interaction, which may be considered useful, can be provided as feedback to the user of the system. Although the descriptions of various embodiments herein may refer to surgical/medical procedures, it will be appreciated that these techniques may be applied in other circumstances, for example manufacturing or fabrication applications where manual procedures are performed on deformable objects.

Referring now to FIG. 1, there is shown a top level system block diagram 100 of one example embodiment consistent with the present disclosure. A light source 102 may be configured to provide linearly polarized light to a polariscope 104 which may provide images of synthetic tissue 106 (a deformable material) that is capable of indicating the stress induced birefringent patterns associated with interactions between a user and the material. Camera 108 may be configured to capture these images and provide them to a machine vision system 110.

Machine vision system 110 may be configured to analyze and classify these interactions by extracting features associated with the birefringent patterns and matching them to features from previously presented (or otherwise pre-defined) images of known interactions, for example during a classifier training period. In some embodiments, the machine vision system 110 may also be configured to track the path of the interaction, for example through a sequence of locations of the interaction with the material 106 over time. The operation of the machine vision system will also be described in greater detail herein. The resulting interaction classifications and/or tracking may then be provided as feedback to the user, for example though a graphical display 112 or other suitable mechanism. The feedback may be provided in real-time and/or stored for subsequent use.

Figure 2:
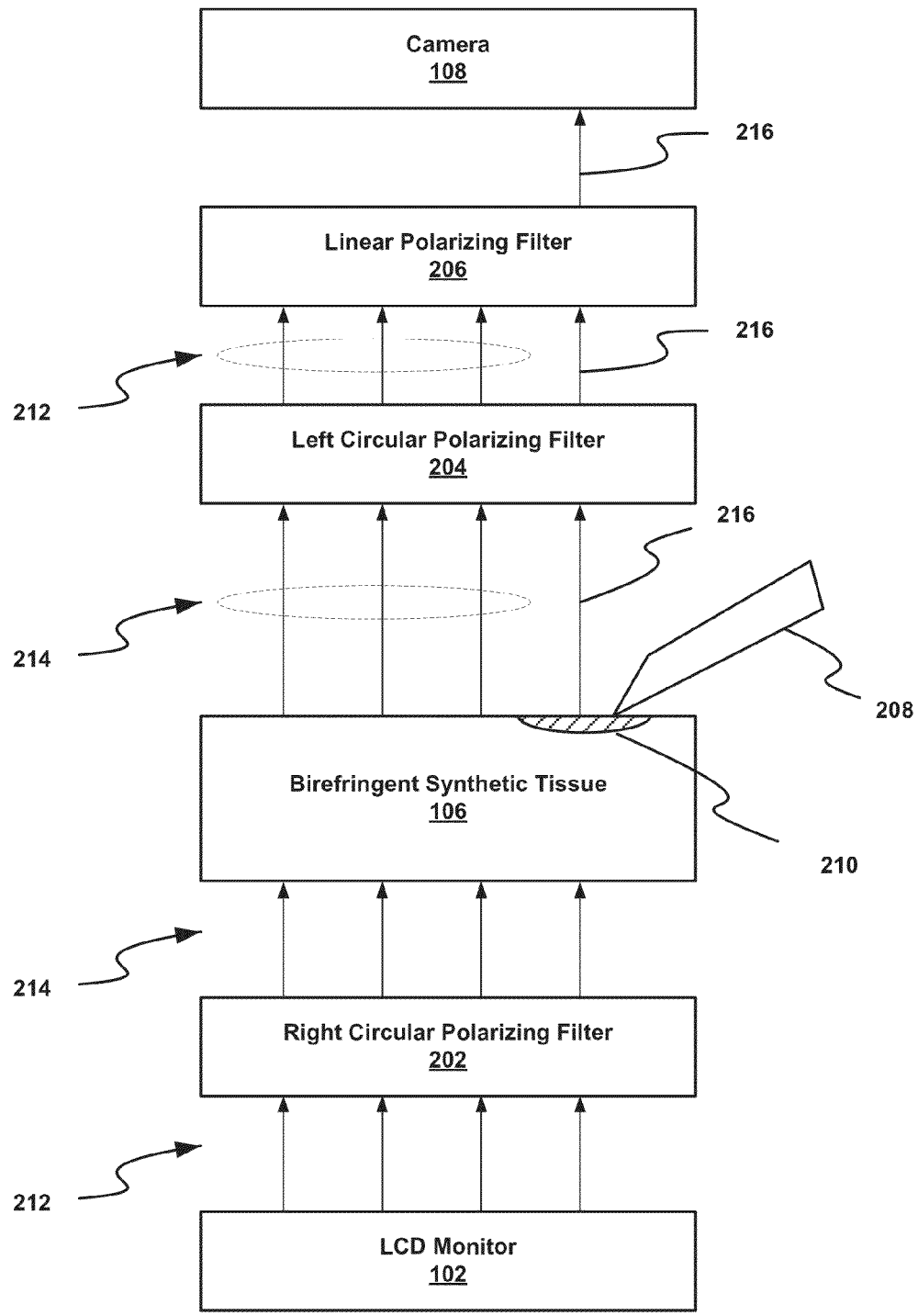
FIG. 2 illustrates a block diagram of one example embodiment consistent with the present disclosure.

FIG. 2 illustrates a block diagram 200 of one example embodiment consistent with the present disclosure. A Liquid Crystal Display (LCD) monitor may be configured as the light source 102 employed to generate linearly polarized light 212 provided to the polariscope 104. The polariscope may include a right circular polarizing filter 202, a left circular polarizing filter 204 and a linear polarizing filter 206 in the arrangement as shown. The right circular polarizing filter 202 may be configured to convert the light provided by the LCD monitor 102 from linear polarization 212 to right circular polarization 214. The right circular polarized light 214 passes through birefringent synthetic deformable tissue 106. A tool, finger, or other object 208 interacts with the tissue 106 creating a deformation region 210 that exhibits an elastic or viscous response. This response causes the light passing through it to be transformed from circular polarization 214 to elliptical polarization 216.

Figure 4:
FIG. 4 illustrates example birefringent images generated by an embodiment consistent with the present disclosure.
Figure 4:
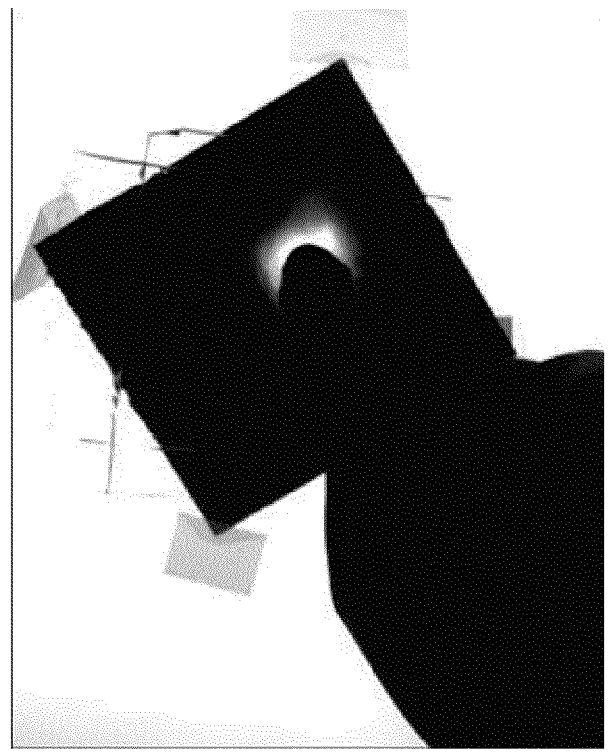

The light transmitted through the tissue 106 then passes through the left circular polarizing filter 204 which may be configured to transform the right circular polarized light 214 back to a linear polarization 212 while leaving the elliptically polarized light 216 unchanged. The linear polarizing filter 206 then filters out the linearly polarized light 212 while allowing the elliptically polarized light 216 to pass through to camera 108 which captures the image. Examples of these images are shown in FIG. 4 where it can be seen that the deformation zone ranges from white through shades of grey (where the elliptically polarized light is allowed to pass to varying extents) while the remainder of the image is substantially black (where the linearly polarized light has been filtered). The camera 108 may then provide the captured image, or series of images taken over time, to the machine vision system 110.

In some embodiments, other suitable light sources may be employed to provide linearly polarized light 212. The circular polarizing filters 202 and 204 may be implemented using quarter-wave crystal waveplates. Alternatively, the circular polarizing filters 202 and 204 may be implemented using quarter wave filters which are typically less expensive. If quarter wave filters are employed, the left circular polarizing filter 204 should be oriented face up and the right circular polarizing filter 202 should be oriented face down.

In some embodiments, additional components, not shown, may be utilized as needed. For example a transparent glass plate may be employed to support the deformable tissue 106 and protect the underlying components from damage due to contact with the object or tools used by the operator. In addition, the deformable tissue may be configured such that a relatively thin layer (e.g. 1-2 mm) may be applied to the deformable material, such as a cellulosic type material, which will deform and also manipulate the polarized light such that the deformation may similarly be detected.

Figure 3:
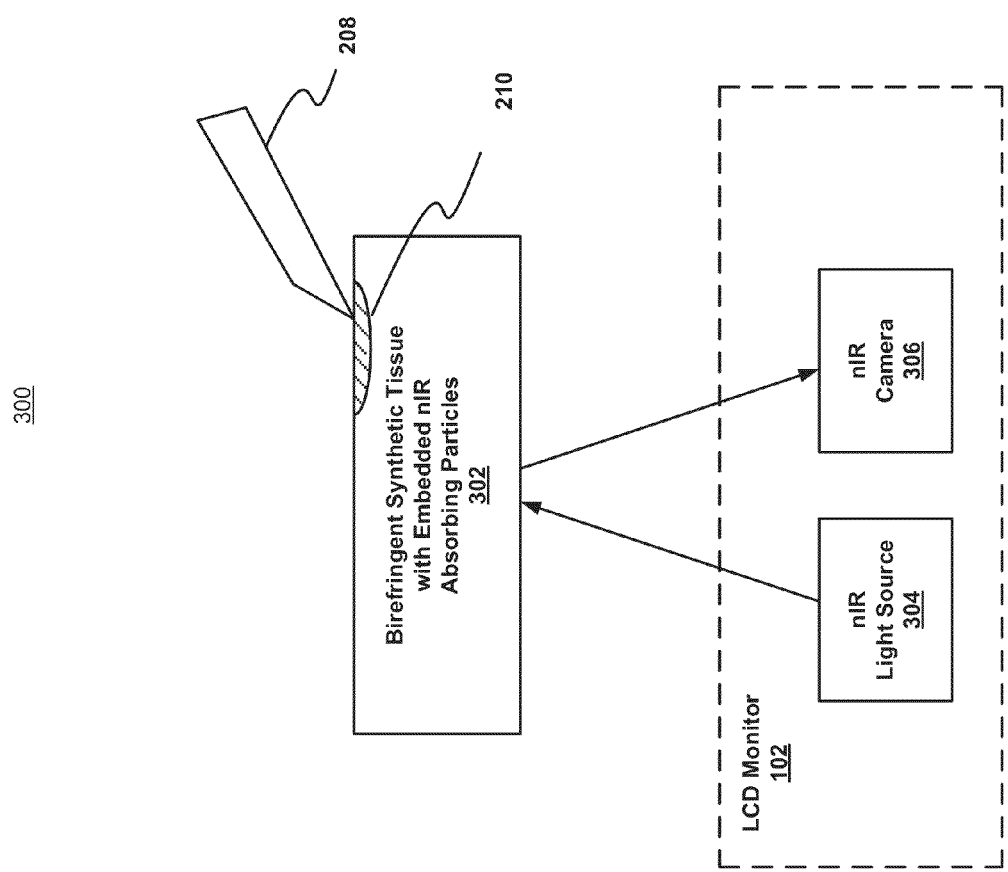
FIG. 3 illustrates a block diagram of another example embodiment consistent with the present disclosure.

FIG. 3 illustrates a block diagram 300 of another example embodiment consistent with the present disclosure. A non-visible light source 304, for example an infrared or near-infrared (nIR) light source, may be configured to illuminate the birefringent synthetic deformable tissue 302. In this embodiment, the tissue 302 may be fabricated with embedded nIR absorbing particles, for example glass micro particles or thermal absorbing powders, that are uniformly distributed through the tissue 302. Variations in the density of the tissue 302, resulting from deformation 210 caused by user interactions with tools 208 or the like, may be detected by nIR camera 306 as variations in reflectivity of the nIR light and captured as an image which may also be processed by machine vision system 110.

The nIR imaging system may be used alone or in combination with the polariscope to create multiple sets of images in different spectral wavelengths that the machine vision system 110 may use to improve pattern detection and recognition capabilities. In some embodiments, the nIR light source 304 and camera 306 may be integrated into the LCD monitor assembly 102, for example through a rearrangement of some of the internal components of the LCD monitor. The nIR light may therefore be emitted through the LCD monitor without affecting the image seen by the user.

FIG. 4 illustrates example birefringent images generated by an embodiment consistent with the present disclosure. FIG. 4(a) shows a birefringent pattern caused by touching the deformable material 106, while FIG. 4(b) shows a birefringent pattern caused by incision using an instrument such as a scalpel on the material. The deformations resulting from these different types of interactions between the user and the material can be seen to generate recognizable patterns that ranges from white through shades of grey (where the elliptically polarized light is allowed to pass to varying degrees) through black (where the linearly polarized light has been filtered). The machine vision system 110 may be configured to identify and classify these recognizable patterns.

The deformable material 106 that is viscoelastic, capable of birefringence and transparent (viewing and observation of an applied deformation by cameras or a user) enables the tracking and detection capability of the machine vision system 110, which processes the images from one or more cameras as the user's hands and instruments interact throughout the depth and breadth of the material. The material may further be configured to be resistant to decomposition. In some embodiments, more complex anatomical structures may be simulated through the integration of multiple layers of material having different densities or other physical characteristics. For example simulated skin material may be layered over simulated muscle material which in turn may be layered over simulated bone material.

Figure 5:
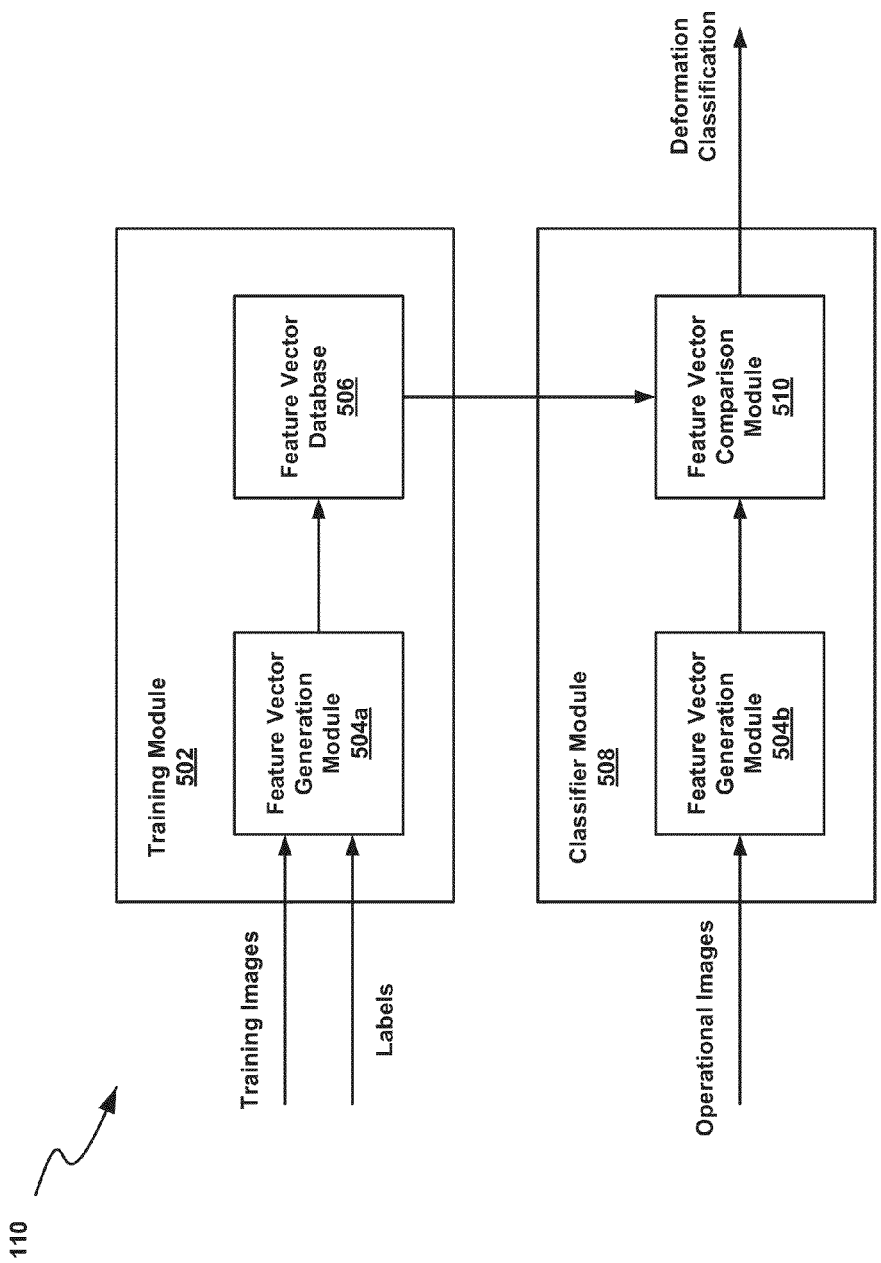
FIG. 5 illustrates a block diagram of another example embodiment consistent with the present disclosure.

The ability to simulate, classify and track an interaction such as an incision may enable the simulation of more complex operations including, but not limited to, for example:
Training to avoid accidental cuts
Finding and cauterizing severed blood vessels
Surgical removal training
Removal of tissue samples for biopsy
Removal of blockages
Removal of eye lens
Cesarean section incision
Debridement of wounded, burned or infected tissue
Tissue grafting
Hernia repair
Suturing incision FIG. 5 illustrates a block diagram of another example embodiment consistent with the present disclosure. Machine vision system 110 is shown to include a training module 502 and a classifier module 508. Training images along with associated labels (for example "scalpel," or "clamp," etc.) are provided to a feature vector generation module 504a which may be configured to generate feature vectors to be stored in a database 506. The training images and associated labels may be provided by a human subject matter expert or other user of the system. Multiple training images may be provided for each type of interaction. For example, a scalpel incision or finger press may be applied at different angles in each training image so that the classifier may recognize the interaction with greater reliability under different conditions. The feature vectors, as will be described in greater detail herein, are extracted/estimated from the training images and may capture characteristics of the image that are useful for identification/recognition of the type of interaction being observed.

The types of interactions that may be classified may include, but not be limited to: incisions, application of clamping pressure, needle puncture, insertion and removal of objects and manual manipulation. The type of tool used in the interaction may also be recognized or identified by the classifier. In some embodiments, the interaction path may also be tracked based on two or more identified locations of the interactions over time. The tracking may further include the determination of pressure, depth and speed of the interaction over the path.

Classifier module 508 may be configured to receive operational images, for example from camera 108 and polariscope 104 and/or from nIR camera 306, of the object of interest being operated on by a user of the system. The operational images are provided to a feature vector generation module 504b which may be configured to generate feature vectors associated with those operational images. A feature vector comparison module 510 may be configured to search for, compare and/or find matches between the feature vectors of the operational image and stored feature vectors in database 506 associated with the training images. If and when a suitable match is found, the deformation pattern associated with the interaction may be classified as corresponding to one of the interactions associated with a training image.

Figure 6:
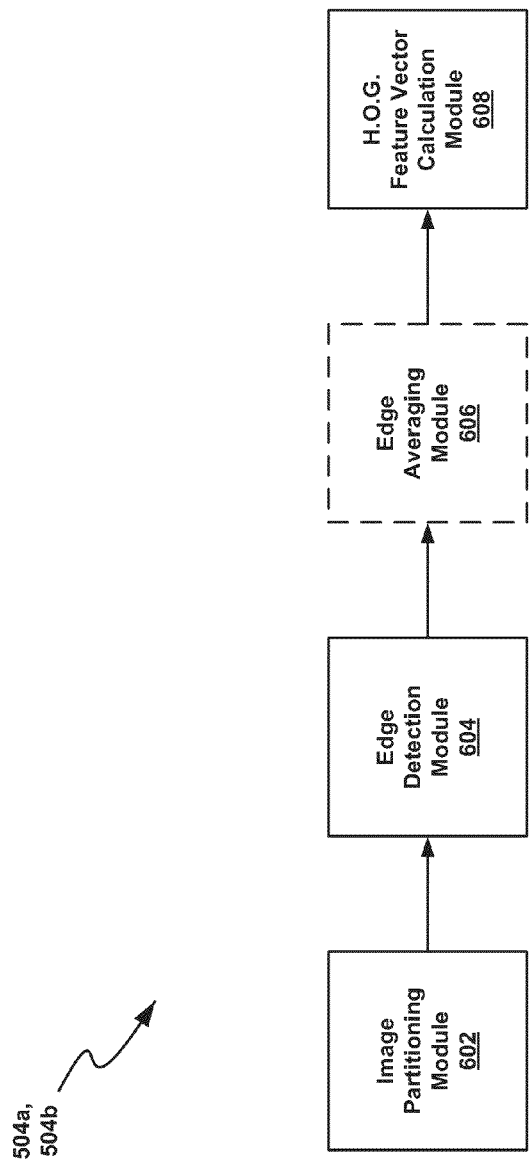
FIG. 6 illustrates a block diagram of another example embodiment consistent with the present disclosure.

FIG. 6 illustrates a block diagram of another example embodiment consistent with the present disclosure. Feature vector generation modules 504a, 504b are shown to include an image partitioning module 602, an edge detection module 604, an edge averaging module 606 and a Histogram of Oriented Gradient (HOG) features vector calculation module 608. The image partitioning module 602 may be configured to determine regions of interest within the image, for example regions encompassing deformation generated patterns, contours or clusters of pixels. This is illustrated, for example, in FIG. 7. During training, as associated with module 504a, the image partitioning module 602 may be guided in the definition of regions by a human subject matter expert who may identify regions of the image that are most useful for classifier recognition. During classifier operation, as associated with module 504b, the image partitioning module 602 may partition the image into regions that correspond to the training defined regions.

Within each region, edge detection module 604 may be configured to identify edges based on changes in image intensity. A Sobel edge detection filter, which calculates a two dimensional image gradient approximation, may be used for this purpose. During training, as associated with module 504a, edge averaging module 606 may be configured to average the detected edges from two or more of the provided training images to reduce noise and improve the classification.

HOG feature vector generation module may be configured to generate feature vectors for each region based on the detected edges. The feature vectors comprise a list of scalar values which serve as a signature that is descriptive of the shape or other characteristics of the interaction. For example, the scalar values may be counts of occurrences of gradient orientation (or edge direction) within each region.

Figure 7:
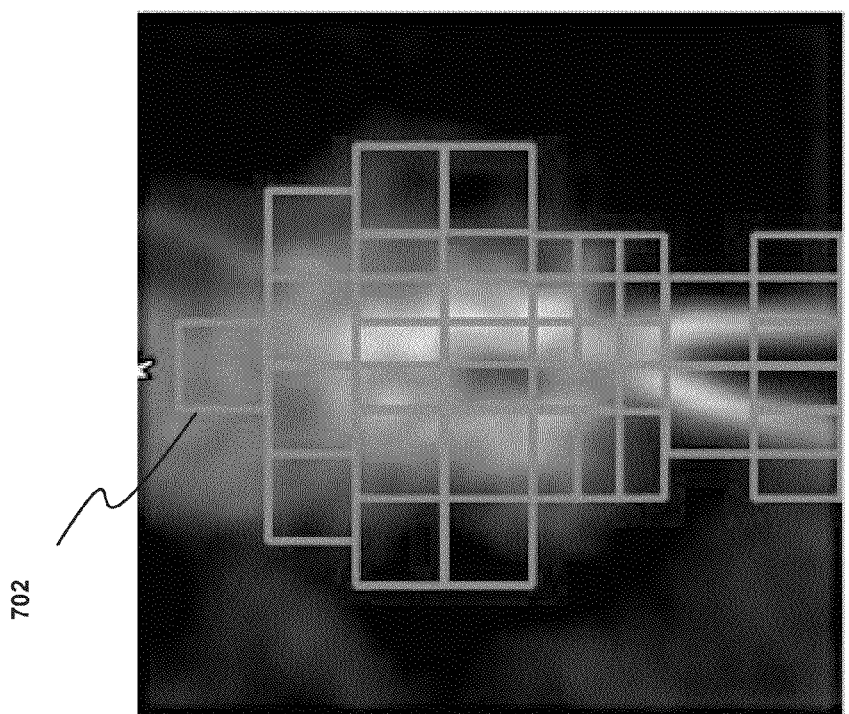
FIG. 7 illustrates image classifier feature regions of an example embodiment consistent with the present disclosure.

FIG. 7 illustrates image classifier feature regions of an example embodiment consistent with the present disclosure. The image associated with an interaction may be partitioned into regions, for example 702, by image partitioning module 602 as described herein. The regions may include portions of deformation generated patterns, contours or clusters of pixels that have been defined or identified by a human subject matter expert during training of the classifier, or through any other suitable means, as being useful for classifier recognition of the given type of interaction.

Figure 8:
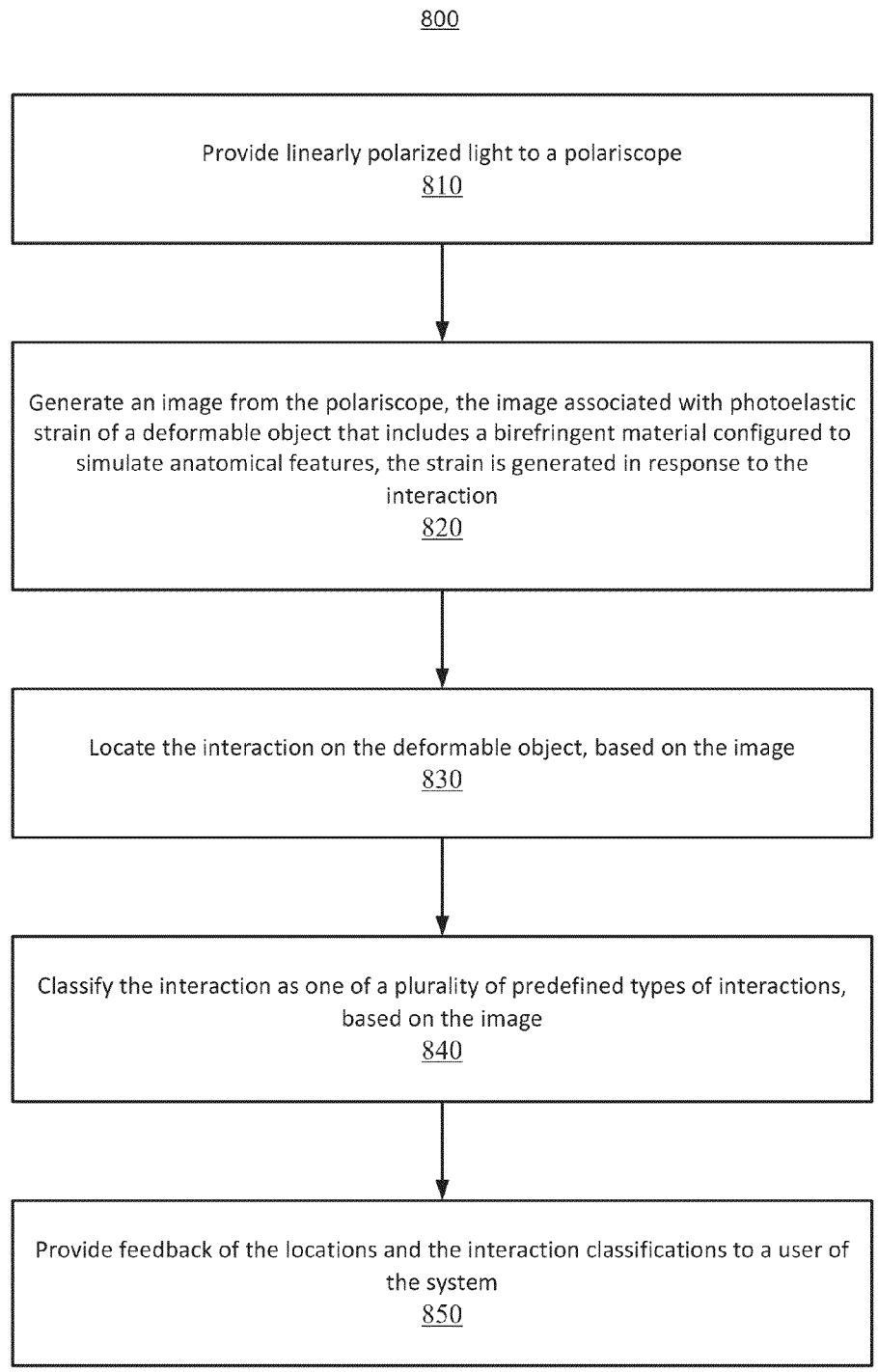
FIG. 8 illustrates a flowchart of operations of another example embodiment consistent with the present disclosure.

FIG. 8 illustrates a flowchart of operations 800 of another example embodiment consistent with the present disclosure. At operation 810, linearly polarized light is provided to a polariscope. At operation 820, an image is generated from the polariscope, the image associated with photoelastic strain of the deformable object. The deformable object comprises a birefringent material configured to simulate anatomical features. The strain is generated in response to the interaction. At operation 840, the interaction is located on the deformable object, based on the image. At operation 840, the interaction is classified as one of a plurality of predefined types of interactions, based on the image. At operation 850, feedback of the locations and the interaction classifications is provided to a user of the system.

In view of the foregoing, it may be appreciated that the present disclosure also relates to an article comprising a non-transitory storage medium having stored thereon instructions that when executed by a machine result in the performance of the steps of the methods as described in the examples above such as, for example, in connection with the description associated with FIG. 8. In some embodiments, the method operations may be implemented in software and executed by a processor or may be implemented in hardware such as, for example, an application specific integrated circuit (ASIC) or field programmable gate array (FPGA).

Figure 9:
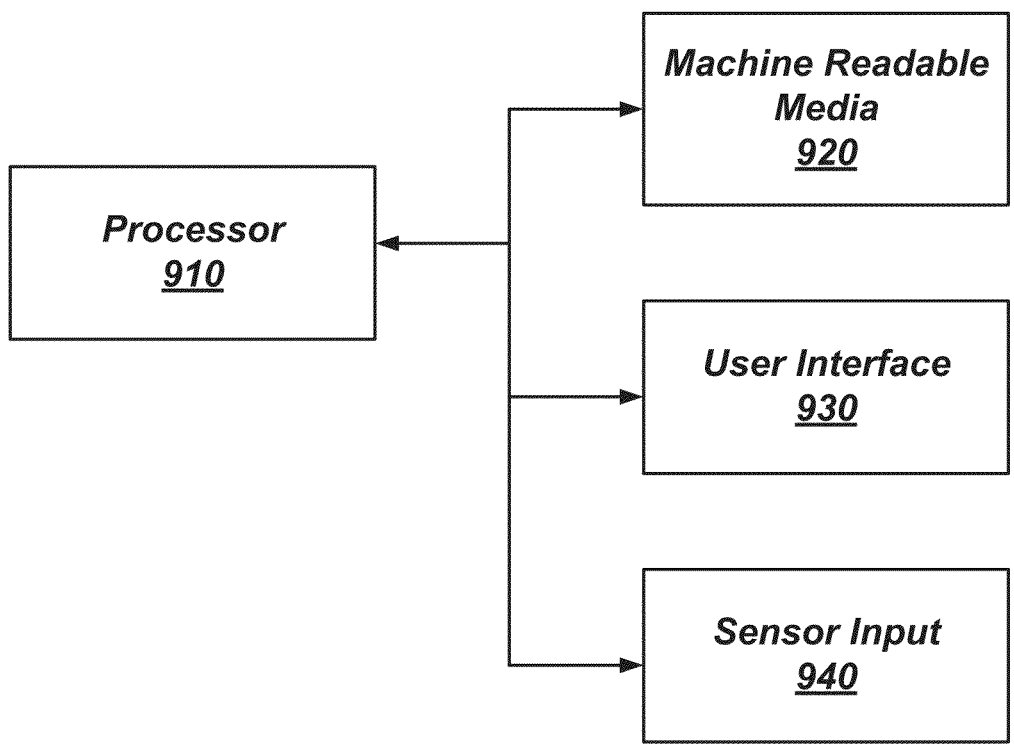
FIG. 9 illustrates a processor, machine readable media, user interface and sensor input that may be employed in an example embodiment consistent with the present disclosure.

It should also be appreciated that the functionality described herein for the embodiments of the present invention may therefore be implemented by using hardware, software, or a combination of hardware and software, as desired. If implemented by software, a processor and a machine readable medium are required. The processor may be any type of processor capable of providing the speed and functionality required by the embodiments of the invention. Machine-readable memory includes any non-transitory media capable of storing instructions adapted to be executed by a processor. Non-transitory media include all computer-readable media with the exception of a transitory, propagating signal. Some examples of such memory include, but are not limited to, read-only memory (ROM), random-access memory (RAM), programmable ROM (PROM), erasable programmable ROM (EPROM), electronically erasable programmable ROM (EEPROM), dynamic RAM (DRAM), magnetic disk (e.g., floppy disk and hard drive), optical disk (e.g. CD-ROM), and any other device that can store digital information. The instructions may be stored on a medium in either a compressed and/or encrypted format. Accordingly, in the broad context of the present invention, and with attention to FIG. 9, the system and method for the herein disclosed machine vision based analysis and tracking of strain in photoelastic materials may be accomplished with a processor (910), machine readable media (920), user interface (930) and sensor input (940).

Thus the present disclosure provides methods and systems for machine vision based analysis and tracking of strain in deformable materials with application to simulation and training for medical or surgical procedures. According to one aspect there is provided a system. The system may include a light source configured to provide linearly polarized light. The system may also include a polariscope configured to receive the linearly polarized light and to generate an image associated with strain of the deformable material, which comprises a viscoelastic birefringent material configured to simulate anatomical features. The strain is generated in response to the interaction. The system may further include a machine vision system configured to operate on the image to locate the interaction on the deformable object and to classify the interaction as one of a plurality of predefined types of interactions. The system may further include a display configured to provide feedback of the locations and the interaction classifications to a user of the system.

According to another aspect there is provided a method. The method may include providing linearly polarized light to a polariscope. The method may also include generating an image from the polariscope, the image associated with strain of the deformable object, which may comprise a viscoelastic birefringent material configured to simulate anatomical features. The strain is generated in response to the interaction. The method may further include locating the interaction on the deformable material, based on the image. The method may further include classifying the interaction as one of a plurality of predefined types of interactions, based on the image. The method may further include providing feedback of the locations and the interaction classifications to a user of the system.

The foregoing description of several methods and embodiments has been presented for purposes of illustration. It is not intended to be exhaustive or to limit the claims to the precise steps and/or forms disclosed, and obviously many modifications and variations are possible in light of the above teaching. It is intended that the scope of the invention be defined by the claims appended hereto.

What is claimed is:

1. A system for analysis of a viscoelastic response in a deformable material, said system comprising:
    a light source configured to provide linearly polarized light;
    a polariscope configured to receive said linearly polarized light and to generate an image associated with a viscoelastic response of said deformable material, wherein said deformable object comprises a viscoelastic, transparent, thermoplastic, birefringent material;
    a machine vision system configured to operate on said image to locate said response on said deformable material and to classify said response as one of a plurality of predefined types of responses; and
    a display configured to provide feedback of said location of said viscoelastic response and classification of said response to a user of said system.

2. The system of claim 1, further comprising:
    a near infrared (nIR) light source configured to illuminate said deformable material;
    an nIR camera configured to generate a second image based on a reflection of said nIR light from said deformable material, wherein said deformable material is impregnated with a plurality of nIR absorbing particles; and
    said machine vision system is further configured to operate on said second image to locate said viscoelastic response on said deformable material.

3. The system of claim 1, wherein said classification types comprise one of a surgical incision, a needle puncture and a clamp pressure.

4. The system of claim 1, wherein said classification types comprise identification of a tool associated with said response.

5. The system of claim 1, wherein said machine vision system is further configured to track a response path, said path defined by a plurality of said locations of said response.

6. The system of claim 5, wherein said tracking further comprises determination of pressure, depth, and speed of said response along said path.

7. The system of claim 1, wherein said light source is a Liquid Crystal Display (LCD) monitor.

8. The system of claim 1, wherein said machine vision system further comprises:
    a training module configured to generate a first set of Histogram of Oriented Gradient (HOG) features based on training images associated with said predefined types of responses; and
    a classifier module configured to generate a second set of HOG features based on said image provided by said polariscope; and
    said classifier module further configured to find a match between said first set of HOG features to said second set of HOG features.

9. The system of claim 1 wherein said deformable material has a density in the range of 1.03 g/cc to 1.07 g/cc.

10. The system of claim 1 wherein said deformable material comprises a thermoplastic block copolymer.

11. The system of claim 10 wherein said deformable material comprises a thermoplastic block copolymer selected from the group consisting of styrene-butadiene-styrene polymers; styrene-isoprene-styrene polymers; styrene-ethylene-butylene-styrene polymers; styrene-ethylenepropylene polymers; styrene-ethylenebutylene polymers; styrene-butadiene polymers; and styrene-isoprene polymers.

12. The system of claim 10 wherein said thermoplastic block copolymers are mixed with a mineral oil or hydrocarbon oil, wherein said oil is present at a level of 78 wt. % to 88 wt. %.

13. A method for analysis of a viscoelastic response in a deformable material, said method comprising:
    providing linearly polarized light to a polariscope;
    generating an image from said polariscope, said image associated with a viscoelastic response of said deformable material, wherein said deformable material comprises a viscoelastic, transparent, thermoplastic birefringent material;
    locating said viscoelastic response on said deformable material, based on said image;
    classifying said response as one of a plurality of responses, based on said image; and
    providing feedback of said location of said viscoelastic response and classification of said response to a user.

14. The method of claim 13, further comprising:
    illuminating said deformable material with near infrared (nIR) light;
    generating a second image based on a reflection of said nIR light from said deformable material, wherein said deformable object is impregnated with a plurality of nIR absorbing particles; locating said interaction on said deformable material, based on said second image; and
    classifying said viscoelastic response, based on said second image.

15. The method of claim 13, wherein said viscoelastic response classification comprises one of a surgical incision, a needle puncture and a clamp pressure.

16. The method of claim 13, wherein said viscoelastic response classification comprises identification of a tool associated with said response.

17. The method of claim 13, further comprising tracking a response path, said path defined by a plurality of said locations of said responses.

18. The method of claim 17, wherein said tracking further comprises determining pressure, depth, and speed of said responses along said path.

19. The method of claim 13, wherein said classifying further comprises finding a match between HOG features generated from training images associated with said predefined types of responses and HOG features generated from said image provided by said polariscope.

20. An article comprising a non-transitory storage medium having stored thereon instructions that when executed by a machine result in the following operations on a deformable material:
   providing linearly polarized light to a polariscope;
   generating an image from said polariscope, said image associated with a viscoelastic response of said deformable material, wherein said deformable material comprises a viscoelastic, transparent, thermoplastic birefringent material;
   locating said viscoelastic response on said deformable material, based on said image;
   classifying said response as one of a plurality of responses, based on said image; and
   providing feedback of said locations and said viscoelastic response to a user of said system.

21. The article of claim 20, further comprising the operations of:
   illuminating said deformable material with near infrared (nIR) light;
   generating a second image based on a reflection of said nIR light from said deformable material, wherein said deformable material is impregnated with a plurality of nIR absorbing particles; locating said interaction on said deformable material, based on said second image; and classifying said response based on said second image.

22. The article of claim 20, wherein said response classification comprise one of a surgical incision, a needle puncture and a clamp pressure.

23. The article of claim 20, wherein said interaction classification comprises identification of a tool associated with said interaction.

24. The article of claim 20, further comprising the operation of tracking a response path, said path defined by a plurality of said locations of said responses.

25. The article of claim 24, wherein said tracking further comprises the operations of determining pressure, depth, and speed of said responses along said path.

26. The article of claim 20, wherein said classifying further comprises the operation of finding a match between HOG features generated from training images associated with said predefined types of responses and HOG features generated from said image provided by said polariscope.

* * * * *